US007978325B2

(12) United States Patent
Adachi

(10) Patent No.: US 7,978,325 B2
(45) Date of Patent: Jul. 12, 2011

(54) BIOCHEMICAL ANALYZER

(75) Inventor: Sakuichiro Adachi, Hachioji (JP)

(73) Assignee: Hitachi High-Technologies Corporation, Tokyo (JP)

( * ) Notice: Subject to any disclaimer, the term of this patent is extended or adjusted under 35 U.S.C. 154(b) by 253 days.

(21) Appl. No.: 12/121,120

(22) Filed: May 15, 2008

(65) Prior Publication Data
US 2008/0285025 A1    Nov. 20, 2008

(30) Foreign Application Priority Data
May 16, 2007    (JP) ................... 2007-129991

(51) Int. Cl.
*G01J 3/04*        (2006.01)
*G01J 3/28*        (2006.01)
(52) U.S. Cl. ........................................ 356/328
(58) Field of Classification Search .......... 356/326, 356/328, 319, 320, 323, 325
See application file for complete search history.

(56) References Cited

U.S. PATENT DOCUMENTS

| 4,253,765 A | 3/1981 | Kato et al. |
| 4,451,433 A | 5/1984 | Yamashita et al. |
| 4,687,329 A | 8/1987 | Schultz |
| 4,896,963 A * | 1/1990 | Kato ............................ 356/328 |
| 5,014,216 A | 5/1991 | Stafford et al. |

FOREIGN PATENT DOCUMENTS

| DE | 19952652 | 4/2001 |
| EP | 121404 | 10/1984 |
| JP | 6-229829 | 8/1994 |
| JP | 2005-049109 | 2/2005 |

OTHER PUBLICATIONS

J. Phys. E.: Instrum., vol. 14, 1981, Wavelength-modulated derivative spectrometer capable of an automatic analyser of environmental air pollutants, T. Izumi et al, pp. 105-112.

* cited by examiner

*Primary Examiner* — F. L Evans
(74) *Attorney, Agent, or Firm* — Mattingly & Malur, P.C.

(57) ABSTRACT

A light amount is increased and an analyzing accuracy can be kept in accordance with an enlargement of a load angle, however, a scattered light tends to be loaded in an analysis accompanying the scattered light and a dynamic range of a concentration which can be measured becomes narrow. A light is dispersed by a light dispersing portion, a load angle of the received light is changed per wavelength, the load angle is made larger in the light of a wavelength having a small light amount, and the load angle is made smaller in the light a wavelength having a large light amount and used for an analysis accompanying a scattered light. Accordingly, it is possible to gain a dynamic range of a concentration which can be measured in the analysis accompanying the scattered light, while increasing the light amount and maintaining the analyzing accuracy.

6 Claims, 7 Drawing Sheets

FIG.1 PRIOR ART
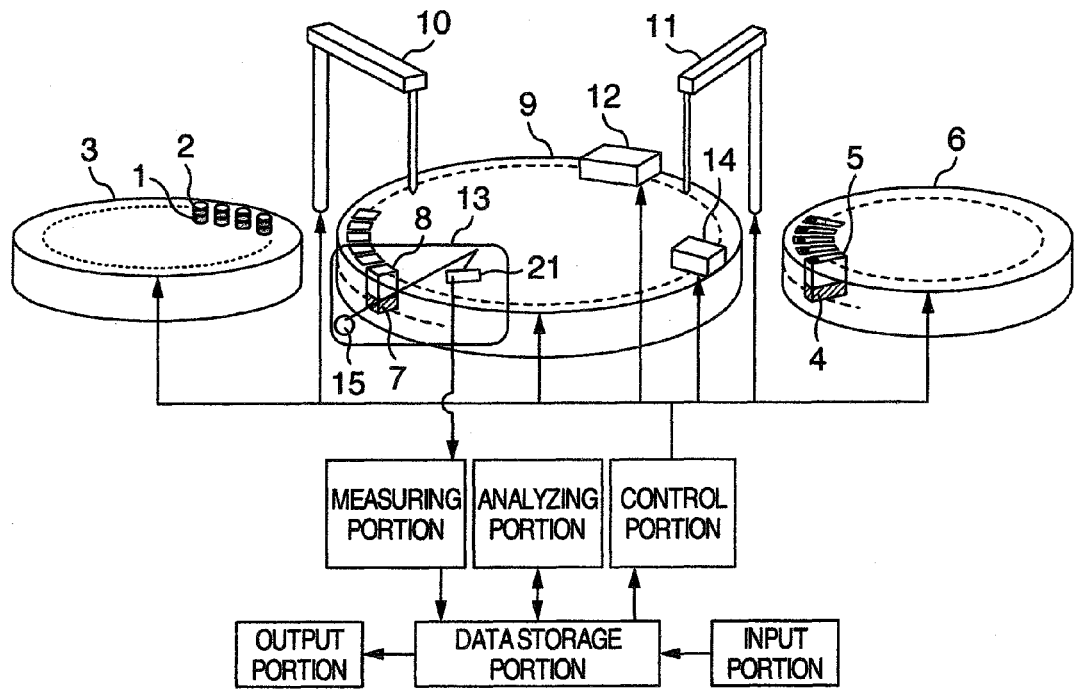
FIG.2 PRIOR ART
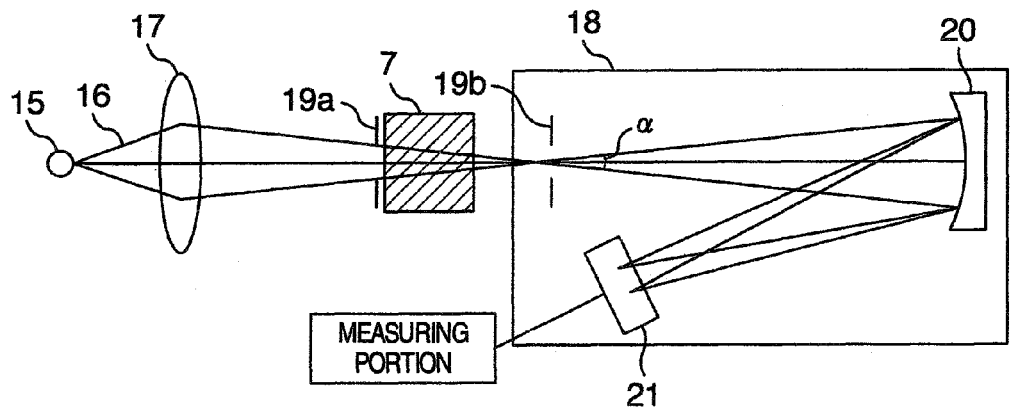

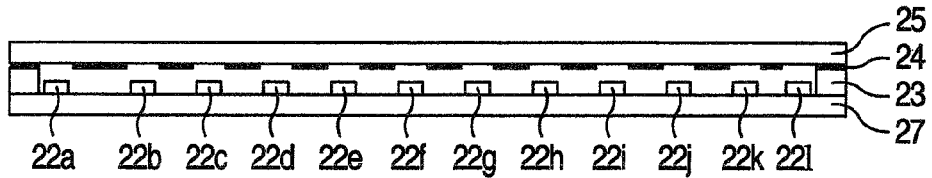
PRIOR ART FIG.3
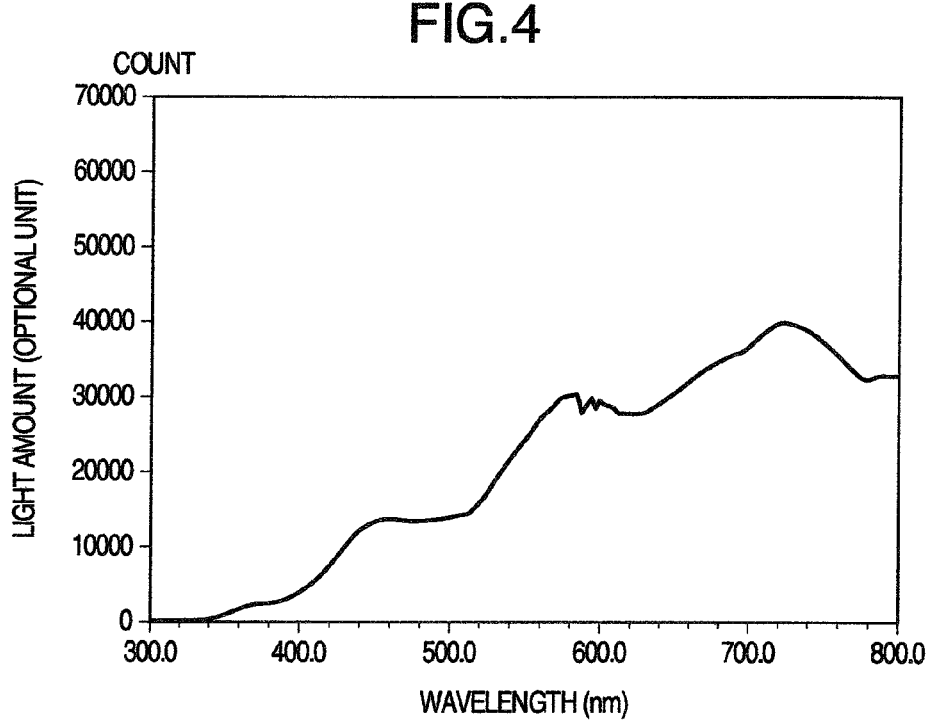
FIG.4
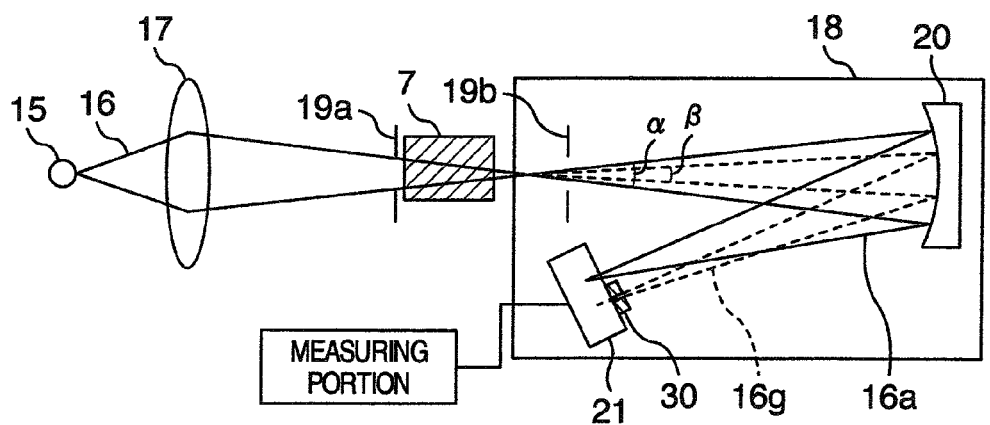
FIG.5

BIOCHEMICAL ANALYZER

PRIORITY CLAIM

The present application claims priority from Japanese application JP-2007-129991 filed on May 16, 2007, the content of which is hereby incorporated by reference into this application.

BACKGROUND OF THE INVENTION (1) Field of the Invention

The present invention relates to a biochemical analyzer analyzing an amount of a component included in a sample, and more particularly to a biochemical analyzer analyzing an amount of a component included in a subject's blood or urine.

(2) Description of Related Art

As the analyzing apparatus analyzing the amount of a component included in a sample, there is a widely used analyzing apparatus which irradiates a light from a light source to a reaction solution in which a sample and a reagent are mixed, and measures an amount of transmitted light having one or more specific wavelengths so as to calculate an absorbance, and determining the amount of the component on the basis of a Lambert-Beer's law (for example, patent document 1 (U.S. Pat. No. 4,451,433)).

In the automatic analyzer, it is necessary to measure an amount of light with respect to many wavelengths corresponding to a number of analytical items. In the automatic analyzer, there has been a light transmitting member transmitting a plurality of dispersed monochromatic lights, a light receiving element array having a light receiving element receiving the monochromatic light passing through the light transmitting member, and a light receiving element array integrally formed in the light transmitting member (for example, patent document 2 (JP-A-6-229829)). Further, there has been a light shielding means which is arranged between a reaction tube and a diffraction grating placed away in a direction of an optical axis of the light transmitting through the reaction tube, and is provided with a through port passing a predetermined range of lights around the optical axis in the transmitted or scattered light (for example, patent document 3 (JP-A-2005-49109)).

FIG. 1 shows a main structure of an automatic analyzer of the prior art for measuring an amount of component included in blood or urine. The automatic analyzer is constituted by a sample cup 2 accommodating a sample 1 in an inner portion, a sample disk 3 in which a plurality of sample cups 2 are arranged, a reagent cup 5 accommodating a reagent 4 in an inner portion, a reagent disk 6 in which a plurality of reagent cups 5 are arranged, a cell 8 mixing the sample 1 and the reagent 4 in an inner portion so as to form a reaction solution 7, a cell disk 9 in which a plurality of cells 8 are arranged, a sample dispensing mechanism 10 which can move the sample 1 from an inner side of the sample cup 2 to an inner side of the cell 8 at a fixed amount, a reagent dispensing mechanism 11 which can move the reagent 4 from an inner side of the reagent cup 5 to an inner side of the cell 8 at a fixed amount, a mixing unit 12 mixing the sample 1 and the reagent 4 within the cell 8, a measuring unit 13 irradiating a light from a light source 15 to the reaction solution 7 so as to disperse the transmitted light and measure an amount of light per wavelength by a light receiving element array 21, a cleaning unit 14 cleaning the cell 8, a control portion controlling each of the apparatus portions mentioned above, a data storage portion storing various data, an input portion which can input a necessary data in the data storage portion from an outer portion, a measuring portion calculating an absorbance from the amount of light, an analyzing portion determining an amount of component from the absorbance, and an output portion which can display the data and can output to the outer portion.

An analysis of an amount of a certain component present in the sample 1 is carried out in accordance with the following procedure. First, the sample 1 within the sample cup 2 is dispensed at a fixed amount into the cell 8 by the sample dispensing mechanism 10. Next, the reagent 4 within the reagent cup 5 is dispensed at a fixed amount into the cell 8. Subsequently, the sample 2 and the reagent 4 within the cell 8 are mixed by the mixing unit 12 so as to form the reaction solution 7. If necessary, a plurality of reagents 4 are additionally dispensed into the cell 8 by the reagent dispensing mechanism 11. The amount of the transmitted light from irradiating the reaction solution 7 is measured by the measuring unit 13, the absorbance is calculated in the measuring portion, and the absorbance data is accumulated in the date storage portion. After the end of the reaction, the inner side of the cell 8 is cleaned by the cleaning mechanism 14 and the next analysis is carried out. In the analyzing portion, the amount of the component is analyzed from the accumulated absorbent data on the basis of an analytical curve data and the Lambert-Beer's law. Data necessary for control and analysis is input to the data storage portion from the input portion. Various data and the results of analysis are displayed and output by an output portion.

FIG. 2 shows a structure of a known conventional measuring unit 13 and measuring portion. A light 16 emitted from the light source 15 is focused by a lens 17, passes through a slit 19a, transmits through the reaction solution 7 and thereafter enters into a dark box 18. The dark box 18 is light shielded so as to prevent the other lights than the light passing through a slit 19b from being incident. The light 16 is dispersed per wavelength by a light dispersing portion 20 after passing through the slit 19b, and enters into the light receiving element array 21. The light receiving element array 21 is connected to a measuring portion. A structure of a known conventional light receiving element array 21 is shown in FIG. 3. A plurality of light receiving elements 22 receiving different wavelengths of the dispersed light are discretely installed on a base table 27. A silicone diode is generally used in the light receiving element 22. In this case, there is shown an example in which twelve light receiving elements 22a to 22l are arranged for receiving twelve different wavelengths of light. A front surface of the light receiving element 22 is provided with a mask 24 for removing a reflected stray light and a color glass filter 25 via a spacer 23. Each of the light receiving elements 22a to 22l is connected to the measuring portion, and transmits a photoelectric current value which is in proportion to the amount of the received light to the measuring portion. The measuring portion converts the photoelectric current value into the absorbance.

In this case, if the amount of the detected light received by the light receiving element 22 is equal to or less than a fixed amount, the precision of the absorbance analysis is lowered by noise such as a dark current or the like except for the photoelectric current. Accordingly, it is necessary to set the amount of the light received by each of the light receiving elements to a fixed amount or more. In the automatic analyzer, it is often the case that the wavelength region from about 340 nm to about 800 nm is used, and a halogen lamp is used for the light source. FIG. 4 is a graph showing a wavelength dependency of the light amount of the halogen light source. As can be appreciated from FIG. 4, in an ultraviolet region which is shorter than 400 nm the light amount becomes small.

In order to increase the analysis precision to a fixed level or higher, it is necessary to design an optical system within the measuring unit in such a manner that a fixed amount or more of light can be secured in the ultraviolet region. In order to secure a light amount equal to or more than the fixed level, it is important to set an acceptance angle (hereafter load angle) of the light received by the light receiving element which is large. A load angle α is shown in FIG. 2. The load angle α is decided by a light beam view showing a state in which the light source is assumed as a point light source and a light emitted from the point light source reaches the light receiving element. For example, as shown in FIG. 2, the load angle is decided by adjusting a distance between an image forming point on which the lights from the point light source converge and a slit 19a, and a width 'a' of the slit 19a. In this case, the load angle in the present specification does not take an influence by a chromatic aberration of a lens or the like into consideration. It is more advantageous to secure the light amount equal to or more than a fixed level in accordance with an increase of the load angle. In this case, in the analysis items of the automatic analyzer, there is an analysis item of scattering the light by using a particle or the like, measuring the amount of the transmitted light other than the scattered light and calculating the absorbance. In the case mentioned above, since an accurate measurement can not be carried out if the light receiving element receives the scattered light, it is necessary that the light receiving element does not receive the scattered light.

It is advantageous for increasing the light amount to make the load angle α larger, however, the scattered light tends to be loaded as well. If the scattered light is loaded, the light receiving element receives extra light, so that a measurable concentration range narrows. In other words, there is a problem that a dynamic range of the measurable concentration decreases. Accordingly, it is important to remove the scattered light in the same manner as securing the light amount. With regard to the problem of the scattered light removal, for example, there is mentioned in patent document 3 a method relating to a removal of a scattered light by a slit. However, in accordance with this method, the load angle becomes small, and there is a problem that it is hard to secure the light having the wavelength in which the light amount is small. From the fact mentioned above, there is needed a method of removing the scattered light while securing a fixed amount or more of the light amount.

As mentioned above, there is a problem that if the load angle is made larger for increasing the light amount, the scattered light is easily loaded, and if the load angle is made smaller for removing the scattered light, the light amount becomes small.

BRIEF SUMMARY OF THE INVENTION

In a biochemical automatic analyzer, after dispersing a light in a light dispersing portion, a load angle is changed per wavelength, the light of a wavelength having a small light amount is set to have a larger load angle, and the light of a wavelength having a larger light amount, particularly used for an analysis accompanying a scattered light is set to have a smaller load angle. The invention is defined by the apparatus of claim 1. The dependent claims relate to preferred embodiments.

As one example, an analyzing apparatus has a cell accommodating a sample, a light source irradiating lights having different light amounts about at least two different wavelengths to the cell, a light dispersing portion dispersing the light transmitting through the cell, and a plurality of light receiving elements receiving the dispersed lights and having different central wavelengths of the detected lights, and a load angle of the light received by the light receiving element is different per the light receiving element.

As another example, an analyzing apparatus has a cell accommodating a sample, a light source irradiating lights having different light amounts about at least two different wavelengths to the cell, a light dispersing portion dispersing the light transmitting through the cell, a plurality of light receiving elements receiving the dispersed lights and having different central wavelengths of the detected lights, and a slit arranged between the light dispersing portion and at least one of the light receiving element.

As another example, an analyzing apparatus has a light source irradiating lights having different light amounts about at least two different wavelengths, a light dispersing portion dispersing the light irradiated by the light source, at least one cell accommodating a sample and onto which the dispersed light dispersed to the light dispersing portion is irradiated, a plurality of light receiving elements receiving the dispersed light passing through the cell and having different central wavelengths of the detected lights, and a slit arranged between the cell and at least one of the light receiving element.

The light source irradiates the lights having the different light amounts of a first wavelength equal to or more than 400 nm and a second wavelength less than 400 nm.

The analyzing apparatus has at least one slit arranged between the light dispersing portion and at least one the light receiving element, the light source irradiates the lights having the different light amounts of a first wavelength equal to or more than 400 nm and a second wavelength less than 400 nm, and the slit is arranged between the light dispersing portion and at least one the light receiving element receiving the light of the first wavelength.

The light source irradiates the lights having the different light amounts of a first wavelength equal to or more than 400 nm and a second wavelength less than 400 nm, and the slit is arranged between the light dispersing portion and at least one the light receiving element receiving the light of the first wavelength.

It is preferable that the light source is constituted by a halogen light source.

It is further preferable that the light dispersing portion is constituted by a diffraction grating.

The slit is arranged between the light dispersing portion and at least one the light receiving element receiving the light having a central wavelength equal to or more than 400 nm.

It is preferable that the slit is arranged so as to face to the light receiving element.

The slit has a through opening portion, and the opening portion is set such that a load angle of the light passing through the opening portion so as to be received becomes equal to or less than a load angle of the light having a central wavelength less than 400 nm.

It is preferable that the analyzing apparatus further has a slit array arranged between the light dispersing portion and the cell.

It is further preferable that the analyzing apparatus further has a slit array arranged between the light receiving portion and the cell, and an optical fiber transmitting the dispersed light from the slit array to the cell.

As one example, there is provided an analyzing system having a particle, a light source irradiating lights having different light amounts about at least two different wavelengths, a light receiving portion dispersing the light passing through the cell, a plurality of light receiving elements receiving the dispersed light and having different central wavelengths of the detected lights, and a slit arranged between the light dispersing portion and at least one the light receiving element.

In the analyzing system, it is preferable that the particle is constituted by a latex particle.

The wavelength having the greater light amount makes the load angle smaller and the wavelength having the smaller light amount makes the load angle larger by changing the load angle per wavelength. Accordingly, it is possible to increase a dynamic range of a concentration which can be measured in an analysis accompanying the scattered light, while maintaining measurement accuracy. The present invention thus becomes an effective means in the case of reducing an amount of the reaction solution.

Other objects, features and advantages of the invention will become apparent from the following description of the embodiments of the invention taken in conjunction with the accompanying drawings.

BRIEF DESCRIPTION OF THE SEVERAL VIEWS OF THE DRAWING

FIG. 1 shows an example of a known structure of an analyzing apparatus;

FIG. 2 shows an example of a known structure of a measuring unit;

FIG. 3 shows an example of a known structure of a light receiving element;

FIG. 4 shows data per wavelength of a halogen light source;

FIG. 5 is a schematic view of a measuring unit in accordance with an embodiment 1 of the present invention;

DETAILED DESCRIPTION OF THE INVENTION

Embodiment 1

In the present embodiment, there is shown a structure in which a slit is arranged only with respect to a specific wavelength between a light dispersing portion and a light receiving element. In accordance with the present structure, it is possible to make a load angle small in the specific wavelength, after dispersing the light by the light dispersing portion. The overall structure is basically the same as the analyzing apparatus shown in FIG. 1, however, the measurement unit 13 is different.

Figure 13:
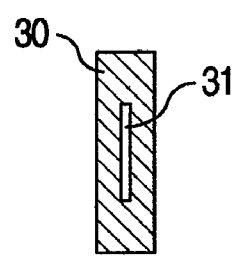
FIG. 13 is an explanatory view of a slit in accordance with the embodiment 1 of the present invention.
Figure 14:
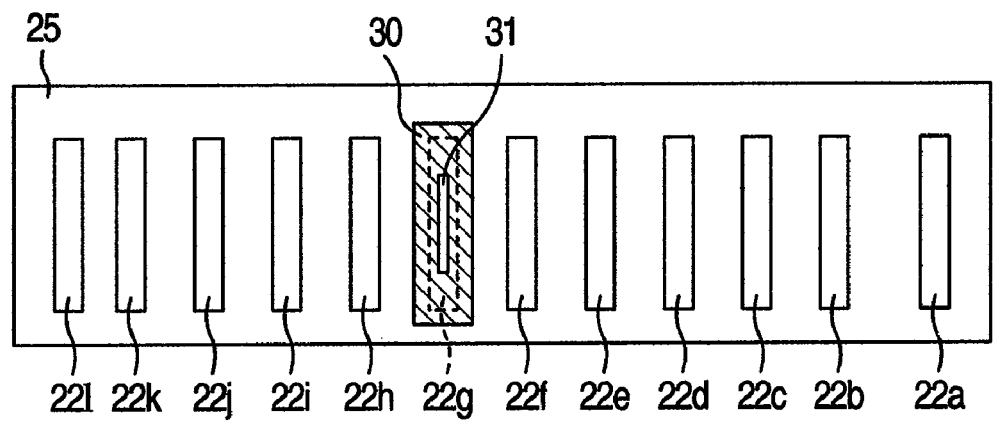
FIG. 14 is a schematic view of the slit and the light receiving array in accordance with the embodiment 1 of the present invention.

FIG. 5 shows an exemplary schematic view of a measuring unit 13 in accordance with the present embodiment. A light 16 emitted from a light source 15 is focused by a lens 17, and enters into a dark box 18 after passing through a slit 19a and transmitting through a reaction solution 7. Within the dark box 18, after the light 16 transmits through a slit 19b and is thereafter dispersed per wavelength by a light dispersing portion 20, the light 16 goes into a light receiving element array 21. In the present embodiment, a reflection type diffraction grating is used in the light dispersing portion 20. Light having a wavelength between 340 nm and 800 nm and used in the automatic analyzer is broadly classified into an ultraviolet light having a wavelength equal to or less than 400 nm and a visible light having a wavelength equal to or more than 400 nm, however, the light source 15 employs a light source emitting the lights having different light amounts with respect to at least two different wavelengths, particularly employs a light source having different light amounts of a first wavelength equal to or more than 400 nm and a second wavelength less than 400 nm in this case. In the present embodiment, a halogen light source is used. A liquid amount of the reaction solution 7 is, for example, 120 μl, and a light having a wavelength of 570 nm, for example, is used for measuring an absorbance in an analysis accompanying a scattered light using a particle. A slit 30 for each wavelength is installed in a front face of the light receiving element array 21. FIG. 13 shows an exemplary structural view of the slit 30 for each wavelength, and FIG. 14 shows an exemplary structural view of the slit 30 and the light receiving element array 21. The slit 30 for each wavelength is provided with an opening portion 31, and is placed so as to oppose a front side in an inverse direction to a forward direction of at least one of the light receiving elements receiving the lights having the wavelength equal to or more than 400 nm, in this case, the light receiving element corresponding to the wavelength of 570 nm, in such a manner as to form an effectively available slit limiting the light after being emitted from the light source until being received by the light receiving element with regard to the light of the wavelength of 570 nm, whereby a load angle β is made smaller for the wavelength of 570 nm while maintaining a load angle α of the light of 340 nm having the smaller light amount. The load angle α of the wavelength of 340 nm is expressed by a solid line and the load angle β of the wavelength of 570 nm is expressed by a dotted line in a light beam view. In other words, the light of the wavelength less than 400 nm having the smaller light amount makes the load angle and the light amount large, while the light of the wavelength equal to or more than 400 nm having the larger light amount makes the load angle and the light amount small, by placing the slit 30 for each wavelength at the front side of at least one of the light receiving elements receiving the lights of the wavelengths equal to or more than 400 nm.

Figure 6:
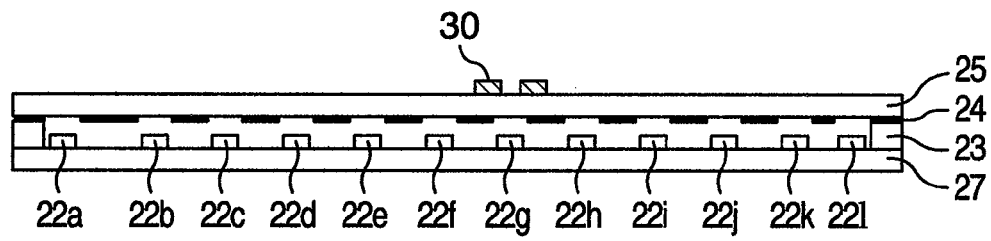
FIG. 6 is a schematic view of a light receiving element array in accordance with the embodiment 1 of the present invention.

FIG. 6 shows the light receiving element array 21 and the slit 30 for each wavelength. A basic structure of the light receiving element array 21 is the same as the basic structure in FIG. 3 for the most part. The corresponding wavelengths are constituted by 340 nm, 405 nm, 450 nm, 480 nm, 505 nm, 546 nm, 570 nm, 600 nm, 660 nm, 700 nm, 750 nm and 800 nm, for example. The slit 30 for each wavelength is provided with respect to the light receiving element 22g corresponding to the wavelength of 570 nm (i.e. a wavelength greater than or equal to 400 nm).

Accordingly, it is possible to make the load angle in the wavelength of 570 nm small while maintaining the load angle of the light of 340 nm having the smaller light amount. A scatterer is stored within the cell, and scatters a portion of incident light. The load angle β is set to about one half as large as α only in the wavelength of 570 nm. Accordingly, it is possible to make the load angle small so as to receive a reduced amount of scattered light. In this case, in the measurement accompanying the scattered light generally using the latex particle or the like as the scatterer, there is often the case that the absorbance of the light equal to or more than 400 nm is measured. As a result, the light amount of 570 nm is dimmed about one quarter in comparison with the case that the slit 30 for each wavelength is not installed. However, since the light amount of 570 nm at least twice as large as the light amount of 340 nm from as shown in FIG. 4, a fixed light amount or more is secured, and analyzing accuracy is not affected. On the other hand, the light amount secured by keeping the load angle α with regard to the light having the wavelength of 340 nm which has a small light amount is a problem. Further, reducing the light equal to or more than 400 nm is based on reducing stray light caused by internal reflections or the like and is effective.

Figure 7:
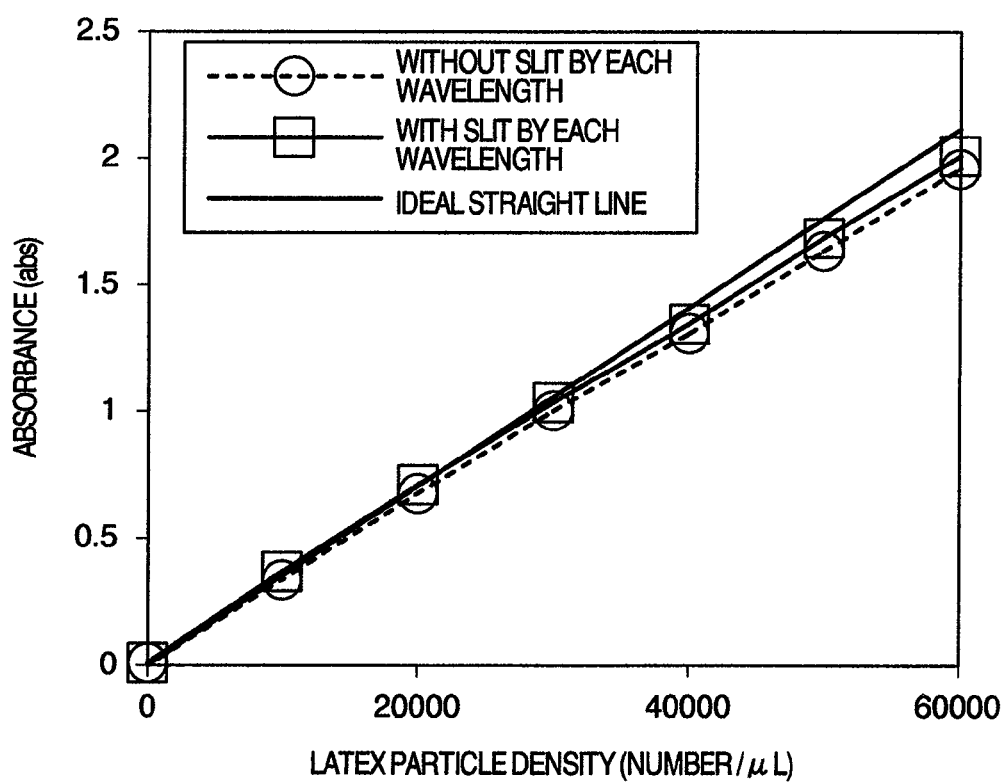
FIG. 7 shows a result of simulation of an absorbance with respect to a concentration of a latex particle in accordance with the embodiment 1 of the present invention.

FIG. 7 shows a magnitude of the absorbance of 570 nm light with respect to latex particle density in the case of a simulation of latex particle in the structure in accordance with the present embodiment. A magnitude of the latex particle is set to 2 v. Setting the density in a horizontal axis and plotting the absorbance on a vertical axis, it is evident that the absorbance is always high and the scattered light is always removed in the case that the slit for each wavelength is provided.

Figure 8:
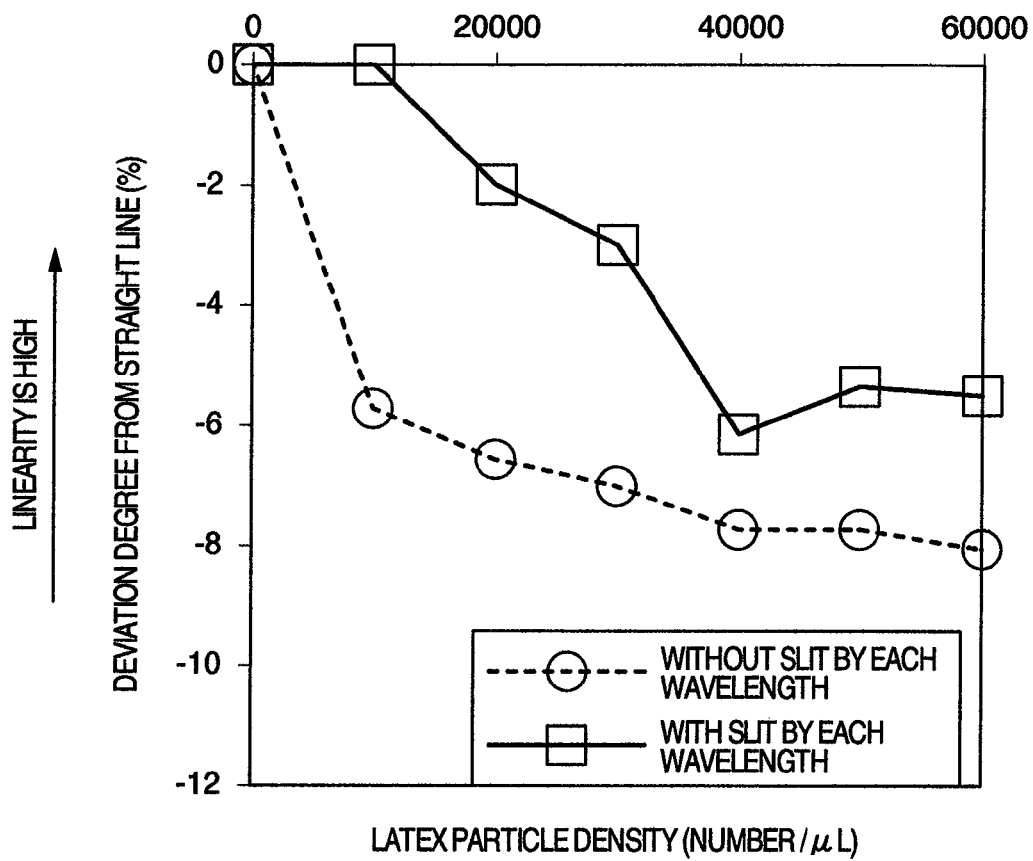
FIG. 8 shows data indicating a deviation from a straight line in the result of simulation in accordance with the embodiment 1 of the present invention.

FIG. 8 shows a magnitude of a deviation from a straight line by a percent rate. As a result of drawing a straight line of an ideal absorbance in the case that the scattered light differs little from the result of FIG. 7, and comparing the magnitude of the deviation between the case that the slit for each wavelength is provided and the case that the slit for each wavelength is not provided, the fact is shown that the deviation is smaller in the case that the slit for each wavelength is provided than the case that the slit for each wavelength is not provided. Accordingly, there is shown a matter that it is possible to improve a dynamic range of a concentration which can be measured.

As mentioned above, it is possible to improve the dynamic range of the concentration which can be measured while keeping the analyzing accuracy by securing the light amount in the wavelength having the smaller light amount, and making the load angle smaller in the wavelength in which it is necessary to remove scattered light.

Further, in accordance with the structure of the present embodiment, it is possible to change the load angle per wavelength, and it is possible to improve the dynamic range of the concentration which can be measured, while keeping the analyzing accuracy.

Particularly, in the case where the light source is a halogen light source, it is possible to suppress the detection of scattered light and it is possible to improve the dynamic range of the concentration which can be measured, by making the load angle of the measured wavelength smaller in the measurement of the light equal to or more than 400 nm while keeping the light amount in the wavelength in the ultraviolet light equal to or less than 400 nm having the smaller light amount. In this case, for analysis items which generally use latex particles or the like as the scatterer, it is frequently the case that the measured light absorbance is greater than or equal to 400 nm.

Embodiment 2

The second embodiment shows a structure in the case that the amount of the reaction solution is reduced. In this case, an area in which the light is irradiated decreases, and it is hard to secure a fixed amount or more of the light amount. For example, in the case that the amount of the reaction solution is reduced by half, on the assumption that an optical path length corresponding to a length of the reaction solution in an optical axis direction is maintained, an irradiation area of the cell comes to one half, and the light amount received by the light receiving element is respectively reduced by half. It is important to make the load angle large for securing the light amount. In the second embodiment, there is shown a structure in which the load angle is made small by arranging the slit with respect to the specific wavelength between the light dispersing portion and the light receiving element while making the load angle larger. The reflection type diffraction grating is used in the light dispersing portion 20. A basic structure of the whole is the same as the first embodiment, however, the measuring unit 13 is different.

Figure 9:
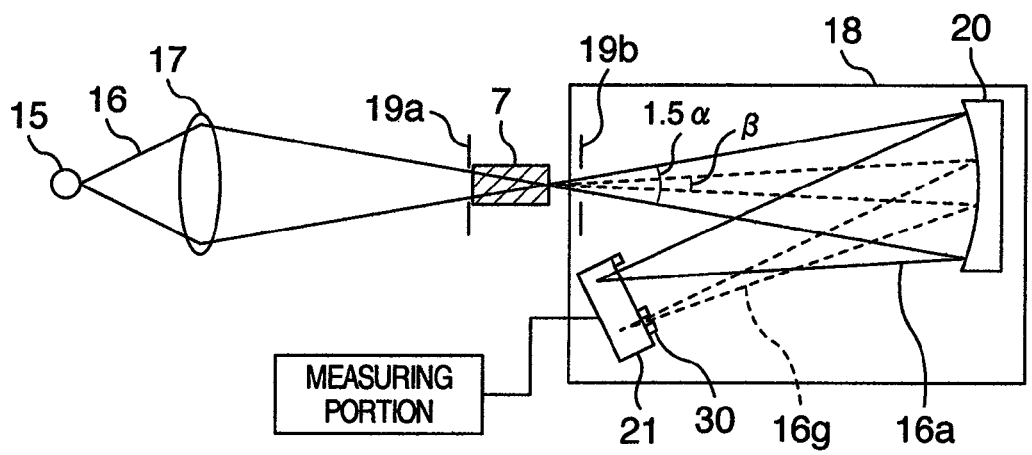
FIG. 9 is an explanatory view of a load angle per wavelength in accordance with an embodiment 2 of the present invention.
Figure 10:
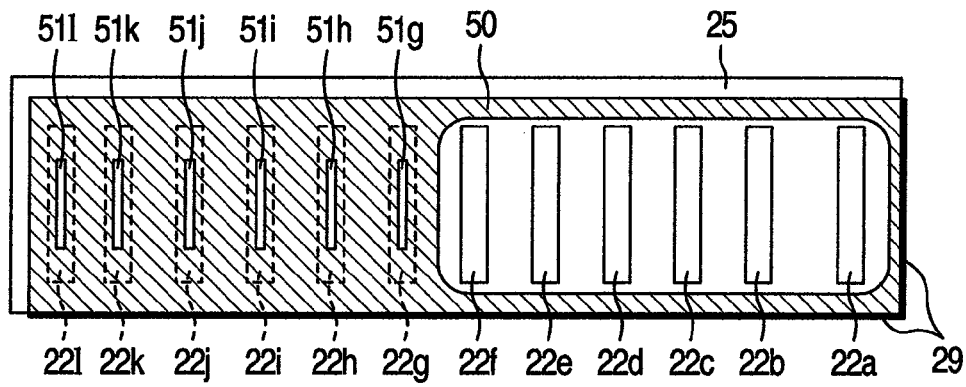
FIG. 10 is a schematic view of a light receiving element array in accordance with the embodiment 2 of the present invention.
Figure 15:
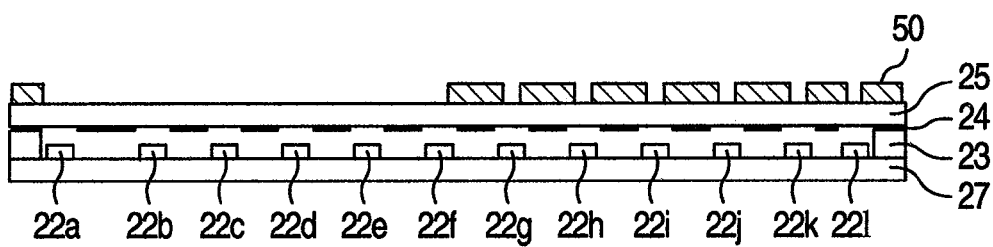
FIG. 15 is a cross sectional view of the light receiving element array in accordance with the embodiment 2 of the present invention.

FIG. 9 shows an exemplary structure of the measuring unit in accordance with the second embodiment. The reaction solution 7 is set to 120 μl in the first embodiment, however, it is set to 60 μl in the second embodiment. In accordance with this, an area of a hole in a center portion of the slit 19a is reduced by about one half in conformity to the irradiated area. However, the load angle α of 340 nm is reduced to half as that in the first embodiment by adjusting a distance between a position on which the lights from the point light source are focused and the slit 19a, and a width of the slit 19a, as shown in FIG. 9. Accordingly, it is possible to secure the light amount while reducing the irradiated area by half. On the other hand, in the load angle β of the light having the wavelength of 570 nm which is used in the measurement of the particle, the scattered light is removed by providing the slit for each wavelength and employing the same structure as in the first embodiment. Therefore, it is possible to maintain the light amount of 340 nm in the same manner as the conventional one while keeping the linear property of the light amount of 570 nm. FIG. 10 shows a view in the case that the light receiving element array is seen from the incident direction of the light, and FIG. 15 shows a cross sectional view of the light receiving element array. A slit member 50 for each wavelength provided with an opening portion 51 is attached to a front surface in direction opposite to a forward moving direction of the light in a color glass filter 25 of the light receiving element array. The slit member for each wavelength is structured such that opening portions 51g-51l are provided in a region corresponding to at least one (six in the example shown in FIG. 10) of the light receiving elements receiving the lights having the wavelengths equal to or more than 400 nm, and no opening portions are provided in a region corresponding to the light receiving elements receiving the lights having wavelengths less than 400 nm. At this time, in order to position a center of a photodiode corresponding to each of the wavelengths and a center of the opening portion, the structure is configured so that the color glass filter is aligned with the light receiving element array. In other words, alignment is provided by setting the slit for each wavelength to the same level of magnitude as the color glass filter.

In the case of reducing the reaction solution amount, it becomes harder to maintain the light amount, particularly for the wavelength in which the light amount is smaller, however, in accordance with the present embodiment, it is possible to maintain the light amount of the wavelength having the smaller light amount by changing the load angle per wavelength, it is possible to remove the scattered light by reducing the load angle in comparison with the wavelength having the smaller light amount in the analysis item accompanying the scattered light. Thereby the dynamic range of the concentration which can be measured can be increased.

Embodiment 3

In the third embodiment, there is shown a system in which the load angle of the light is changed for each wavelength on the basis of a focal distance of the lens, in the biochemical analyzer for measuring absorbance by inputting the light emitted from the light source to the dark box, dispersing the light by the diffraction grating serving as the light dispersing portion, and thereafter inputting the light dispersed by wavelength to the cell accommodating the reaction solution. A basic structure of a whole of the analyzing apparatus is the same as the first embodiment, however, the measuring unit 13 is different.

Figure 11:
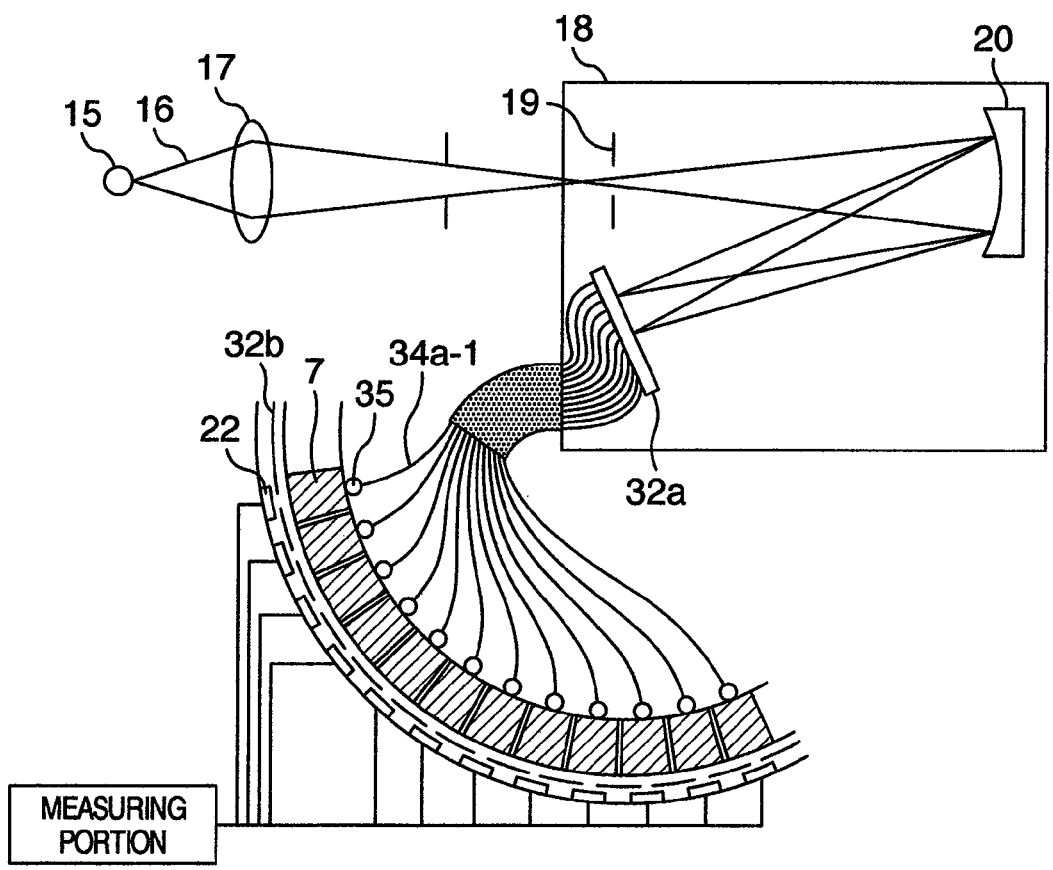
FIG. 11 is a schematic view of a measuring unit in accordance with an embodiment 3 of the present invention.
Figure 16:
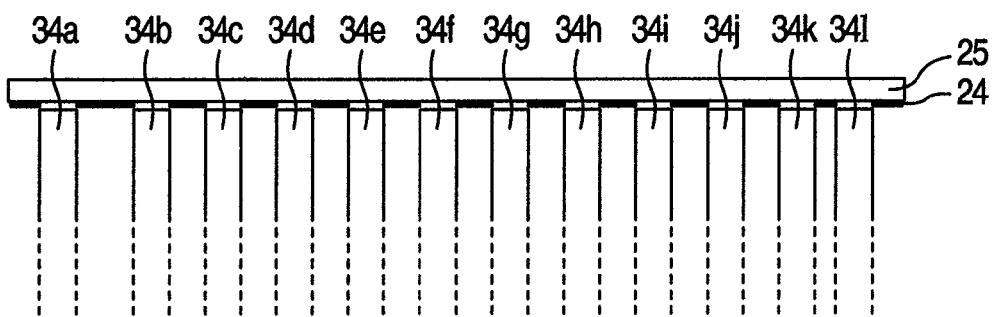
FIG. 16 is an explanatory view of a slit array in accordance with the embodiment 3 of the present invention.

FIG. 11 shows a structure of the measuring unit 13. The measuring unit is constituted by the light source 15, the lens 17, the dark box 18, the light dispersing portion 20, a slit array 32a, optical fibers 34a to 34l, a fiber lens 35, the reaction solution 7, a slit array 32b, and the light receiving element 22. The light 16 emitted from the light source 15 is focused by the lens 17 so as to be incident from the slit 19b in the dark box, is thereafter dispersed by the reflection type diffraction grating serving as the light dispersing portion 20, passes through the slit array 32a provided so that the light having the specific wavelength can be emitted to a position at which the light receiving element array 21 is installed, and is incident to the optical fiber 34. FIG. 16 shows an exemplary structure of the slit array 32a. The light dispersed by the diffraction grating passes through the color glass filter, passes through the stray light removing mask 24 and thereafter enters into the optical fibers 34a to 34l. The light passing through the optical fibers is incident to the reaction solution 7 after passing through the fiber lens 35, and is received by the slit array 32b and the light receiving element 22.

Figure 12:
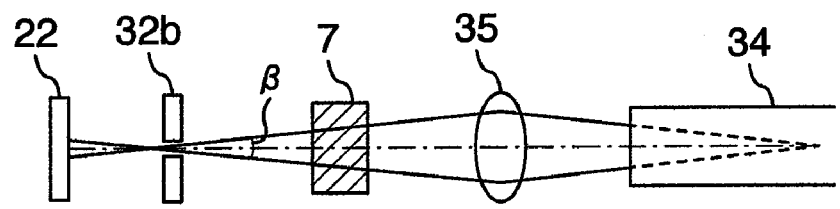
FIG. 12 is an explanatory view of a load angle in accordance with the embodiment 3 of the present invention.

FIG. 12 shows a load angle in the third embodiment. The load angle of the light receiving element is determined by an irradiating angle after being emitted from the fiber lens 35. A position of the fiber lens is adjusted such that the load angle comes to β only in the wavelength of 570 nm which is used for measurement. The load angle is set to α with regard to the other wavelengths, and the light amount is secured even in the wavelength equal to or less than 400 nm. In the system which irradiates the light to the reaction solution after dispersing the light by the diffraction grating as mentioned above, it is possible to change the light receiving angle by adjusting the focal distance or the like of the lens before irradiating the light per each of wavelengths to the reaction solution.

In accordance with the third embodiment, even in the structure in which the light is irradiated to the reaction solution after the light dispersion, it is possible to maintain the light amount of the wavelength having the smaller light amount by changing the load angle per wavelength, and it is possible to remove the scattered light by maintaining the wavelength in the analysis item accompanying the scattered light, and thereby the dynamic range of the concentration which can be measured can be improved.

It should be further understood by those skilled in the art that although the foregoing description has been made by referring to the foregoing embodiments of the invention, the invention is not limited thereto and various changes and modifications may be made without departing from the scope of the appended claims.

The invention claimed is:

1. An analyzing apparatus comprising:
   a cell for accommodating a sample;
   a light source for irradiating light having different light amounts of a first wavelength equal to or more than 400 nm and a second wavelength less than 400 nm to said cell;
   a light dispersing portion for dispersing the light transmitted through said cell;
   a plurality of light receiving elements receiving the dispersed light and having different central wavelengths; and
   a slit arranged between said light dispersing portion and at least one of said light receiving elements,
   wherein an open portion of said slit is set such that a load angle of the light of the first wavelength passing through the open portion that is to be received is less than a load angle of the light of the second wavelength.

2. The apparatus of claim 1, wherein said light source is a halogen light source.

3. The apparatus of claim 1, wherein said light dispersing portion is a diffraction grating.

4. The apparatus of claim 1, wherein said slit is arranged facing said light receiving element.

5. The apparatus of claim 1, wherein said slit includes a first slit array arranged between said light dispersing portion and said cell.

6. The apparatus of claim 5, further comprising an optical fiber for transmitting said dispersed light from said first slit array to said cell, and
   wherein said slit is further includes a second slit array arranged between said light receiving elements and said cell.

* * * * *